United States Patent
Beer et al.

(10) Patent No.: US 8,399,070 B2
(45) Date of Patent: Mar. 19, 2013

(54) METHOD OF DEFINING ELECTRODES USING LASER-ABLATION AND DIELECTRIC MATERIAL

(75) Inventors: Greg P. Beer, Cassopolis, MI (US); Andrew J. Edelbrock, Granger, IN (US)

(73) Assignee: Bayer HealthCare LLC, Tarrytown, NY (US)

(*) Notice: Subject to any disclaimer, the term of this patent is extended or adjusted under 35 U.S.C. 154(b) by 0 days.

(21) Appl. No.: 13/488,882

(22) Filed: Jun. 5, 2012

(65) Prior Publication Data

US 2012/0244295 A1 Sep. 27, 2012

Related U.S. Application Data

(62) Division of application No. 12/679,059, filed as application No. PCT/US2008/078532 on Oct. 2, 2008, now abandoned.

(60) Provisional application No. 60/997,785, filed on Oct. 5, 2007.

(51) Int. Cl.
*B05D 3/00* (2006.01)
*C12Q 1/00* (2006.01)
(52) U.S. Cl. .................. 427/555; 204/403.11
(58) Field of Classification Search .............. 427/555, 427/2.13; 204/520, 401, 403.1, 403.11, 409
See application file for complete search history.

(56) References Cited

U.S. PATENT DOCUMENTS

| | | | |
|---|---|---|---|
| 4,549,454 A | 10/1985 | Yamashita | |
| 5,503,719 A * | 4/1996 | Foos et al. | 205/782.5 |
| 6,531,040 B2 * | 3/2003 | Musho et al. | 204/401 |
| 6,662,439 B1 | 12/2003 | Bhullar | |
| 2005/0016846 A1 | 1/2005 | Groll et al. | |
| 2005/0072670 A1 | 4/2005 | Hasegawa et al. | |
| 2005/0123443 A1 | 6/2005 | Fujiwara et al. | |
| 2007/0135698 A1 | 6/2007 | Shah et al. | |
| 2009/0159197 A1 | 6/2009 | Edelbrock | |

FOREIGN PATENT DOCUMENTS

| | | |
|---|---|---|
| EP | 1 482 307 A | 12/2004 |
| JP | 2003-254933 | 9/2003 |
| JP | 2003-254934 | 9/2003 |
| WO | WO 03/012422 A1 | 2/2003 |
| WO | WO 2007/070486 A2 | 12/2006 |
| WO | WO 2007/075936 A2 | 7/2007 |

OTHER PUBLICATIONS

Written Opinion corresponding to International Patent Application No. PCT/US2008/078532, European Patent Office, dated Dec. 8, 2008, 5 pages.
International Search Report corresponding to International Patent Application No. PCT/US2008/078532, European Patent Office, dated Dec. 8, 2008, 3 pages.

* cited by examiner

*Primary Examiner* — Dah-Wei Yuan
*Assistant Examiner* — Nga Lueng V Law
(74) *Attorney, Agent, or Firm* — Nixon Peabody LLP

(57) ABSTRACT

A method of forming an electrochemical test sensor includes providing a base. Electrochemically-active material is placed on the base. Dielectric material is applied over the electrochemically-active material. A first selected area of the dielectric material is laser-ablated to expose the electrochemically-active material. A second selected area of the dielectric material and the electrochemically-active material are laser-ablated to expose the base. The first selected area is different from the second selected area. A second layer is applied to assist in forming a channel in the test sensor. The channel assists in allowing a fluid sample to contact a reagent located therein. The dielectric material is located between the base and the second layer.

8 Claims, 17 Drawing Sheets

METHOD OF DEFINING ELECTRODES USING LASER-ABLATION AND DIELECTRIC MATERIAL

CROSS-REFERENCE TO RELATED APPLICATIONS

This application is a divisional of U.S. application Ser. No. 12/679,059 filed on Mar. 19, 2010; U.S. application Ser. No. 12/679,059 is the national phase of PCT/US2008/078532 filed on Oct. 2, 2008, that claims priority back to U.S. Provisional Application No. 60/997,785, filed on Oct. 5, 2007, all of which are incorporated by reference in their entireties.

FIELD OF THE INVENTION

The present invention generally relates to a method of forming a test sensor. More specifically, the present invention generally relates to a method of forming an electrochemical test sensor that is adapted to assist in determining a concentration of an analyte by using laser ablation.

BACKGROUND OF THE INVENTION

The quantitative determination of analytes in body fluids is of great importance in the diagnoses and maintenance of certain physiological abnormalities. For example, lactate, cholesterol and bilirubin should be monitored in certain individuals. In particular, it is important that diabetic individuals frequently check the glucose level in their body fluids to regulate the glucose intake in their diets. The results of such tests can be used to determine what, if any, insulin or other medication needs to be administered. In one type of blood-glucose testing system, test sensors are used to test a sample of blood.

A test sensor contains biosensing or reagent material that reacts with blood glucose. One type of electrochemical test sensor is a multilayer test sensor that includes a base or substrate and a lid. Another type of electrochemical test sensor includes a base, a spacer and a lid. Existing electrochemical test sensors include at least two electrodes in the form of an electrode pattern. A potential is applied across these electrodes and a current is measured at the working electrode. The current measurement is directly proportional to the size of the working electrode.

The accuracy of the electrochemical test sensor is typically improved if the area of the working electrode can be precisely defined in the test-sensor manufacturing process. Currently, an electrode pattern (including the working electrode) is typically defined on a base on one axis by the electrode-defining technique (i.e., printing or laser-ablation) and the other axis is defined by a second layer (a lid or a spacer) that is attached to the base. The act of attaching the base and the lid or spacer often has high, less desirable tolerances. For example, the laminating of the base and the lid or spacer tends to have variances that are less than desirable (i.e., +/−0.005 in.). The use of laser-ablation, on the hand, has a more desirable tolerance (i.e., +/−0.0005 inch). Thus, the tolerance in the lid or spacer placement then becomes the significant factor influencing the precision of forming the working-electrode area.

Therefore, it would be desirable to use a method that improves the accuracy of the test-sensor-based system by better defining the working electrode. It would also be desirable to enhance the within-lot reproducibility of the manufacturing process.

SUMMARY OF THE INVENTION

According to one method, an electrochemical test sensor is formed that includes providing a base. Electrochemically-active material is placed on the base. The electrochemically-active material is laser-ablated to form an electrode pattern. Dielectric material is placed over the electrode pattern. Selected areas of the dielectric material are laser-ablated to expose a portion of the electrode pattern. A second layer is applied to assist in forming a channel in the test sensor. The channel assists in allowing a fluid sample to contact a reagent located therein. The dielectric material is located between the base and the second layer.

According to another method, an electrochemical test sensor is formed that includes providing a base. An electrode pattern is formed on the base. Dielectric material is applied over the electrode pattern. Selected areas of the dielectric material are laser-ablated to expose a portion of the electrode pattern. A second layer is applied to assist in forming a channel in the test sensor. The channel assists in allowing a fluid sample to contact a reagent located therein. The dielectric material is located between the base and the second layer.

According to a further method, an electrochemical test sensor is formed that includes providing a base. Electrochemically-active material is placed on the base. Dielectric material is applied over the electrochemically-active material. A first selected area of the dielectric material is laser-ablated to expose the electrochemically-active material. A second selected area of the dielectric material and the electrochemically-active material are laser-ablated to expose the base. The first selected area is different from the second selected area. A second layer is applied to assist in forming a channel in the test sensor. The channel assists in allowing a fluid sample to contact a reagent located therein. The dielectric material is located between the base and the second layer.

BRIEF DESCRIPTION OF THE DRAWINGS

FIG. 1b is a side view of the electrochemical test sensor of FIG. 1a.

FIG. 1c is a top view of the base to be used in the electrochemical test sensor of FIG. 1a.

FIG. 2b is a side view of the electrochemical test sensor of FIG. 2a.

DETAILED DESCRIPTION OF ILLUSTRATED EMBODIMENTS

The present invention is directed to a method of improving the accuracy of an electrochemical test-sensor-based system. The present invention is also directed to enhancing the within-lot reproducibility of the manufacturing process. More specifically, the present invention is directed to improving accuracy and precision of the test-sensor-based system by better defining the electrode pattern using a laser-ablation act.

By better defining the electrode pattern, more precise readings of an analyte concentration are obtained.

The present invention is directed to also improving the accuracy of not only the electrode pattern, but also of the conductive leads and the test sensor contacts. The defining of the electrode pattern and, more specifically, the working electrode area also may reduce product cost, while at the same time reducing the volume of the fluid sample. The cost and the volume of the sample are reduced because of the accuracy of the edge quality in the electrode pattern. By having a more accurate defined area, the working electrode area may be smaller, which leads to a reduced amount of chemistry and fluid sample to be used in the analysis.

The electrochemical test sensors are adapted to receive a fluid sample and be analyzed using an instrument or meter. The test sensor assists in determining the concentrations of analytes. Analytes that may be measured include glucose, cholesterol, lipid profiles, microalbumin, urea, creatinine, creatine, fructose, lactate, or bilirubin. It is contemplated that other analyte concentrations may be determined. The analytes may be in, for example, a whole blood sample, a blood serum sample, a blood plasma sample, other body fluids like ISF (interstitial fluid) and urine, and non-body fluids.

The electrochemical test sensors to be made using the inventive process include at least a base, an electrochemically-active conductive layer for the electrodes, dielectric material and a second layer such as a lid and/or a spacer. In one embodiment, the electrochemical test sensors include a base, an electrochemically-active conductive layer for the electrodes, dielectric material and a lid. In another embodiment, the electrochemical test sensors include a base, an electrochemically-active conductive layer for the electrodes, dielectric material, a spacer and a lid.

The base, spacer and lid may be made from a variety of materials such as polymeric materials. Non-limiting examples of polymeric materials that may be used to form the base, spacer and lid include polycarbonate, polyethylene terephthalate (PET), polystyrene, polyimide, and combinations thereof. It is contemplated that the base, spacer and lid may be independently made of other materials. The electrochemically-active surface on the base may be made from a variety of conductive materials including, but not limited to, carbon, gold, platinum, palladium or combinations thereof.

Figure 1A:
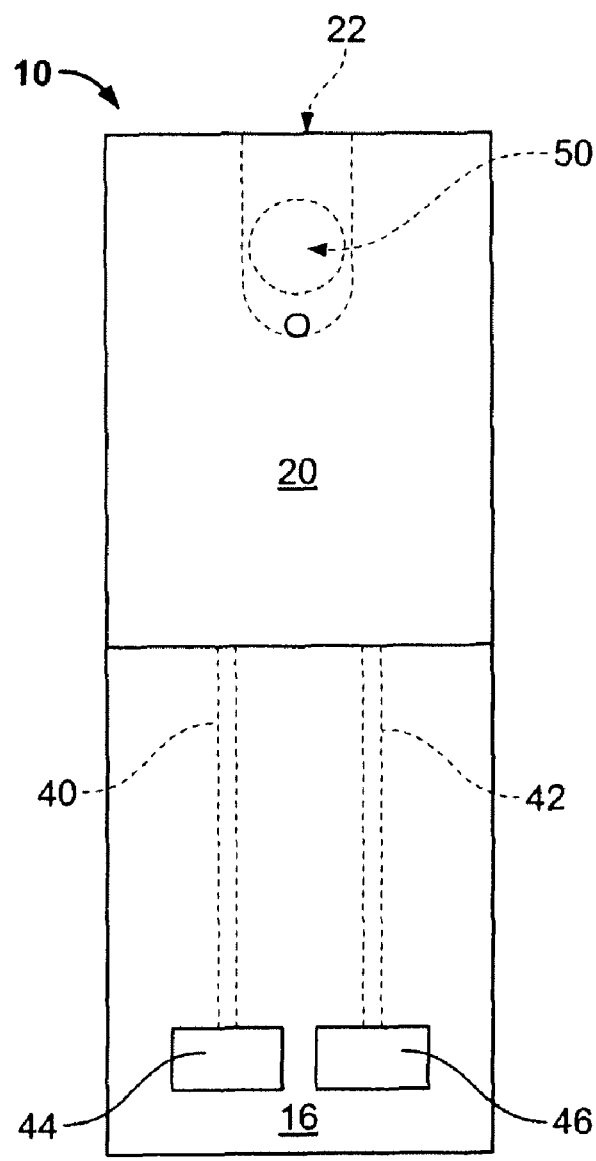
FIG. 1a is a top view of an electrochemical test sensor according to one embodiment.
Figure 1B:
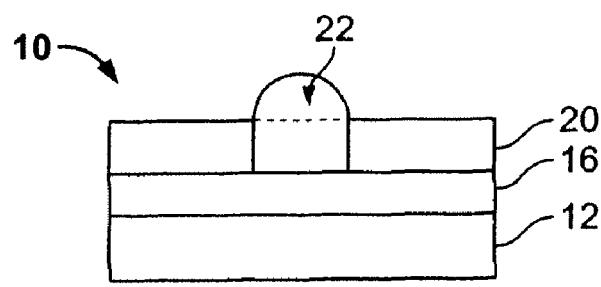
Figure 1C:
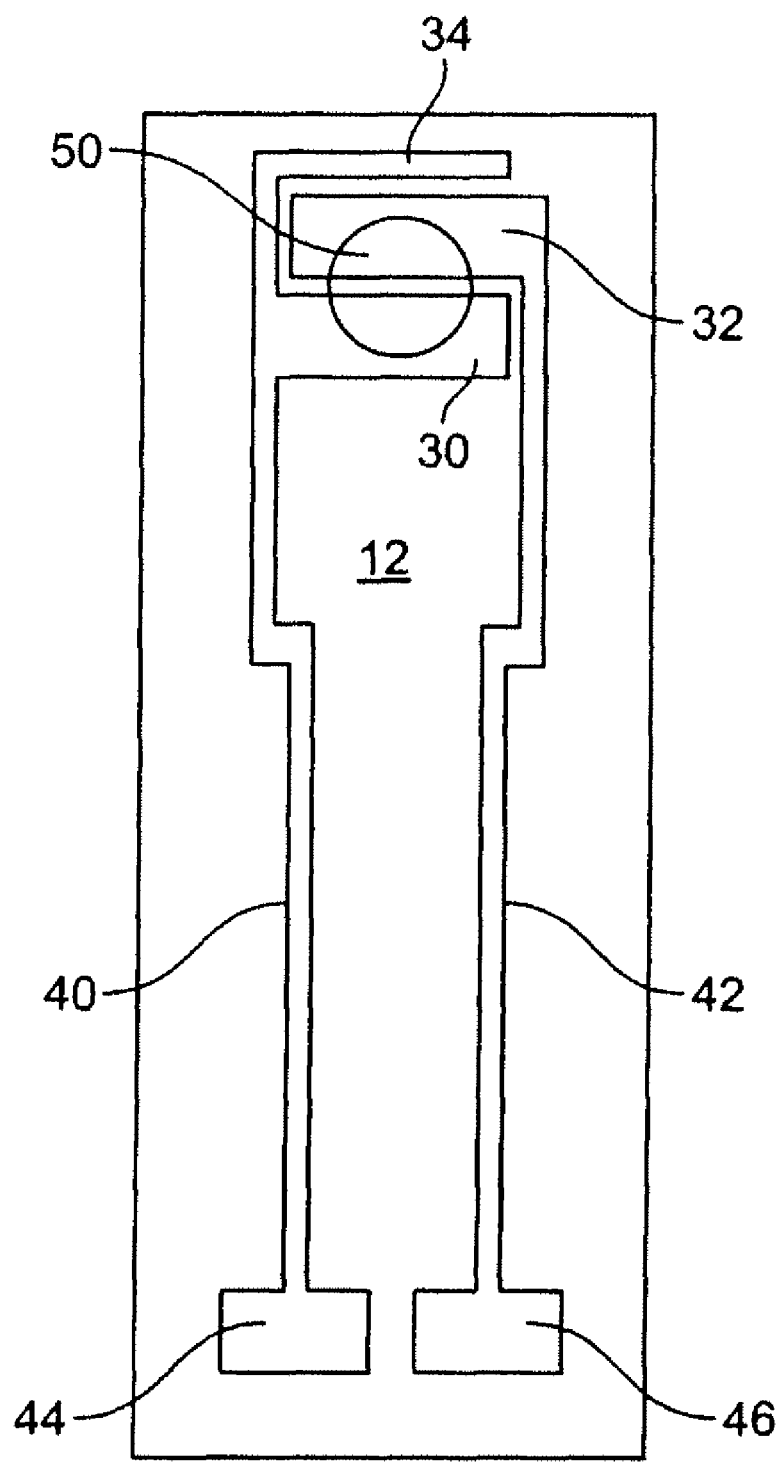

One non-limiting example of an electrochemical test sensor is shown in FIGS. 1a-1d. FIGS. 1a, 1b depict an electrochemical test sensor 10 that includes a base 12 with conductive material, dielectric material 16 and a lid 20. FIG. 1c depicts the base 12 without dielectric material and a lid. Referring back to FIG. 1b, a channel 22 (e.g., capillary channel) is formed when the base 12 and the lid 20 are attached to each other. The capillary channel 22 provides an enclosed flow path for introducing the sample into the test sensor 10 and eventually contacting the electrodes 30, 32, 34 and, thus, forms a reaction zone.

As shown in FIG. 1a, the test sensor 10 includes a reactive or fluid-receiving area 50 that contains an enzyme. The enzyme is selected to react with the desired analyte or analytes to be tested so as to assist in determining an analyte concentration of a fluid sample. The reactive area 50 includes a reagent for converting an analyte of interest (e.g., glucose) in a fluid test sample (e.g., blood) into a chemical species that is electrochemically measurable, in terms of the electrical current it produces, by the components of the electrode pattern.

The reagent typically contains an enzyme (e.g., glucose oxidase), which reacts with an analyte (e.g., glucose) and with an electrochemical mediator (e.g., ferricyanide) to produce an electrochemically measurable species that can be detected by the electrodes. The reactive area 50 may comprise a polymer, an enzyme, and an electron acceptor. The reactive area 50 also may include additional ingredients such as a buffer and a surfactant in some embodiments of the present invention. It is contemplated that other enzymes may be used to react with glucose such as glucose dehydrogenase. If the concentration of another analyte is to be determined, an appropriate enzyme is selected to react with the analyte.

The base 12 of FIG. 1c includes conductive material and, more specifically, a plurality of electrodes 30, 32, 34, a plurality of conductive leads or traces 40, 42 and test-sensor contacts 44, 46. The plurality of electrodes of FIG. 1c includes at least a counter electrode 30 and a working electrode 32 according to this embodiment. The working electrode measures the current when a potential is applied across the working and counter electrodes. The counter electrode should be sufficiently large so as to support the reaction occurring at the working electrode. The applied voltage may be referenced to the reagent deposited adjacent to the counter electrode.

Other electrodes such as a trigger electrode 34 are shown in FIG. 1c. It is contemplated that other electrodes may be used. For example, an electrochemical test sensor may include a detection electrode that detects an underfill condition. The electrochemical test sensor may also include a hematocrit electrode that assists in correcting for the bias that occurs with selected hematocrit concentrations. Additional electrodes include, but are not limited to, electrodes that detect other analytes or species that may potentially interfere with the measurement of the desired analyte. Also, a second working electrode that assists in determining the concentration of another analyte may be used.

It is contemplated that more or less electrodes can be formed in the method of the present invention. For example, the electrochemical test sensor may include exactly two electrodes or at least three electrodes. The exactly two electrodes may be a working electrode and a counter electrode in which an electrochemically created current flow when these electrodes are electrically connected and a potential is created between them.

The electrodes are formed of conductive materials such as, for example, metallic materials (e.g., gold, platinum, palladium, rhodium, ruthenium, or combinations thereof) or carbon. Examples of components of electrochemical test sensors, including their operation, may be found at, for example, U.S. Pat. No. 6,531,040. It is contemplated that other components of electrochemical test sensors may be used other than that disclosed in, for example, U.S. Pat. No. 6,531,040.

The dielectric material assists in insulating electrochemically-active material on the base. The dielectric material may be made from a variety of materials and methods such as, for example, sputtered dielectric coatings (e.g., titanium aluminum nitride, titanium dioxide and silicon dioxide), slot-die coating, gravure printing, spin coating, screen-printed polymeric materials solutions or inks (e.g., fluorinated polymers, parylene polymers and acrylics). It is contemplated that other dielectric materials may be used such as other commercially available dielectric coatings.

Figure 2A:
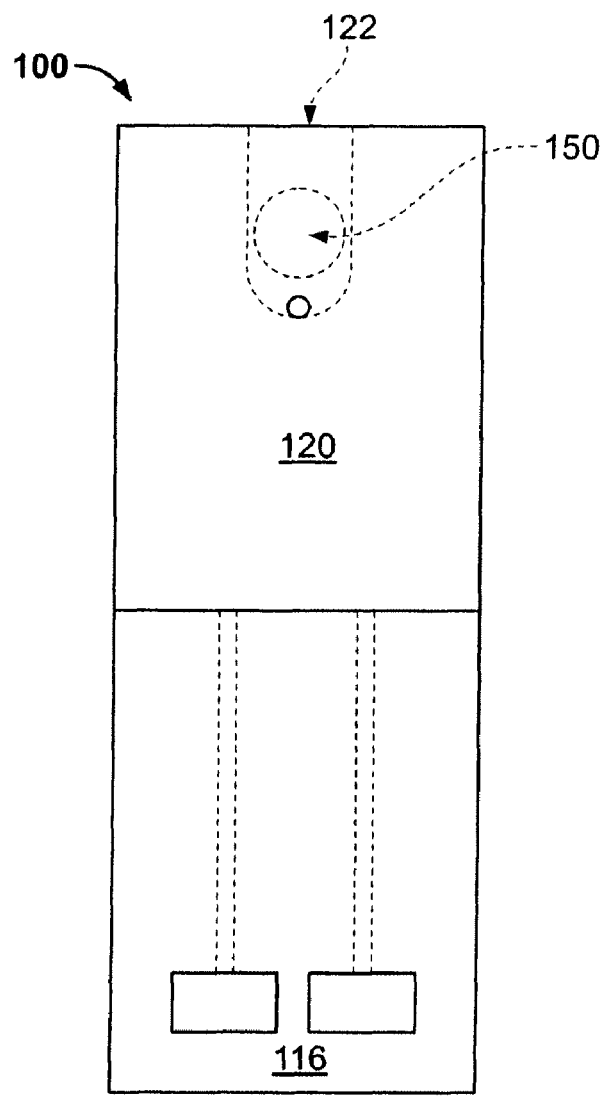
FIG. 2a is a top view of an electrochemical test sensor according to another embodiment.
Figure 2B:
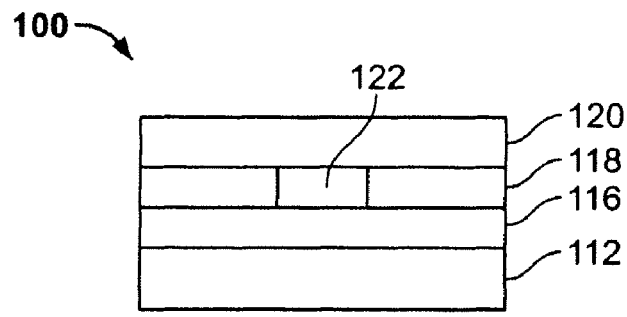

Another non-limiting example of an electrochemical test sensor is shown in FIGS. 2a, 2b. FIGS. 2a, 2b depict an electrochemical test sensor 100 that includes a base 112 with conductive material, dielectric material 116, a spacer 118 and a lid 120. The base 112 and the dielectric material 116 may be the same or similar to the base 12 and the dielectric material 16 discussed above. A channel 122 (e.g., capillary channel) is formed when the base 112, the dielectric material 116, the spacer 118 and the lid 120 are attached to each other. The capillary channel 122 provides an enclosed flow path for introducing the sample into the test sensor 100 and eventually contacting the electrodes and, thus, forms a reaction zone.

The electrodes formed on the base 112 may be the same as described above with respect to the base 12. The electrodes include a counter and working electrode in one embodiment. In other embodiments, the electrodes may include additional electrodes such as the above discussed trigger electrode, detection electrode, hematocrit electrode, a second working electrode and other electrodes.

The present invention is directed to an inventive process for forming an electrochemical test sensor. In one method, the electrochemical test sensors may be formed from ribbon strips. The ribbon strips may be made from processes such as a multiple-sheet process or a web process. For example, in an embodiment with a base, dielectric material, spacer and lid, a base-ribbon strip, a dielectric-ribbon strip, a spacer-ribbon strip and a lid-ribbon strip may be used. For improved efficiency, the electrochemical test sensors are generally formed after all of the ribbon strips have been attached. In another embodiment, the base-ribbon strip is adapted to be attached (e.g., laminated) with a second layer such as, for example, a lid-ribbon strip.

According to one method, an electrochemical test sensor is formed. The method includes providing a base and placing electrochemically-active material on the base. The electrochemically-active material is laser-ablated to form an electrode pattern. Dielectric material is applied over the electrode pattern. Selected areas of the dielectric material are laser-ablated to expose a portion of the electrode pattern. A second layer is applied to assist in forming a channel (e.g., a capillary channel) in the test sensor. The capillary channel assists in allowing a fluid sample to contact a reagent located therein.

The electrochemically-active material is placed or located on the base and is generally from about 50 to about 500 Angstroms (Å) in thickness and, more typically, from about 150 to about 350 Angstroms (Å) in thickness. The electrochemically-active material may be located on the base using, for example, physical vapor deposition (e.g., sputtering), chemical vapor deposition (cvd), screen printing or a laminated metallic foil.

The electrode pattern may be defined by using a mask and a laser such as, for example, an Excimer laser, solid state, YAG (singled, doubled or tripled frequency) or a carbon dioxide-based laser. One example of a mask is a chrome-on-glass mask in which a beam of light is only allowed to pass through selected areas.

According to another method, the electrode pattern may be formed with a laser using direct writing of the lines. In a method using a laser with direct writing of the lines, a laser beam of light is moved so as to define the electrode pattern. The laser may define, for example, the plurality of electrodes, the conductive leads and the meter contacts. Lasers that produce a beam of energy capable of removing a layer and that can be moved to form an electrode pattern may be used in this method. Non-limiting examples of such lasers are carbon dioxide-based lasers and all yttrium-based lasers such as yttrium aluminum garnet (YAG) lasers.

After the electrode pattern has been formed in this method, the dielectric material is applied to insulate the electrode pattern. The dielectric material may be applied by methods such as physical vapor deposition (e.g., sputtering), chemical vapor deposition (cvd), spin coating, slot-die coating, reverse roll, or printing (e.g., gravure or screen printing).

A second laser ablation is used to remove selected areas of the dielectric material to expose a portion of the electrode pattern. Thus, in this process, the entire electrode area used for the electrochemical detection of an analyte is defined by laser ablation of the dielectric material. The second laser ablation also may expose the test-sensor contacts.

In other embodiments, the test-sensor contacts may be formed by a first laser ablation or a printed conductive layer to attach to conductive leads made from the laser ablation. In another embodiment, the test-sensor contacts may be formed by a mask that blocks this area from the dielectric coating. Depending on the dielectric material, the second laser ablation act may be performed in a similar or the same manner as the laser-ablation act that forms the electrode pattern from the electrochemically-active material. For example, the first and second laser-ablation acts may be performed at different intensities and/or using a different number of pulses. It is contemplated that the separate laser-ablation acts may be performed uses different characteristics/features.

In one process, the reagent may be applied to the electrode surfaces. The reagent may be applied to the electrode surface by, for example, gravure or screen printing, microdepositing (e.g., ink-jet spraying) and coating (e.g., slot coating). The reagent may also be located on other surfaces such as dielectric material or a second surface such as a lid or spacer. In any of these embodiments, the reagent would need to contact the fluid sample, such as by using a capillary channel.

The base is then attached to a second layer. In one embodiment, the base is attached to a lid. As discussed above, the base and the lid may be in the form of respective ribbon strips. In another embodiment, the base is attached to a spacer. As discussed above, the base and the spacer may be in the form of respective ribbon strips. According to another embodiment, the second layer may be a spacer-lid combination. The spacer-lid combination may be in the form of a ribbon strip (combination of spacer-ribbon strip and lid-ribbon strip) that has been previously formed before being attached to the base-ribbon strip. If ribbon strips are used, the test sensors may be excised using a mechanical punch or other methods.

The base may be attached to the second layer (e.g., lid or spacer) using, for example, a pressure-sensitive adhesive and/or a hot melt adhesive. Thus, the attachment between the base and the second surface uses pressure, heat or the combination thereof. It is contemplated that other materials may be used to attach the base to the second surface. It is also contemplated that the base and the second surface may be attached using ultrasonic energy or solvent welding.

Figure 3A:
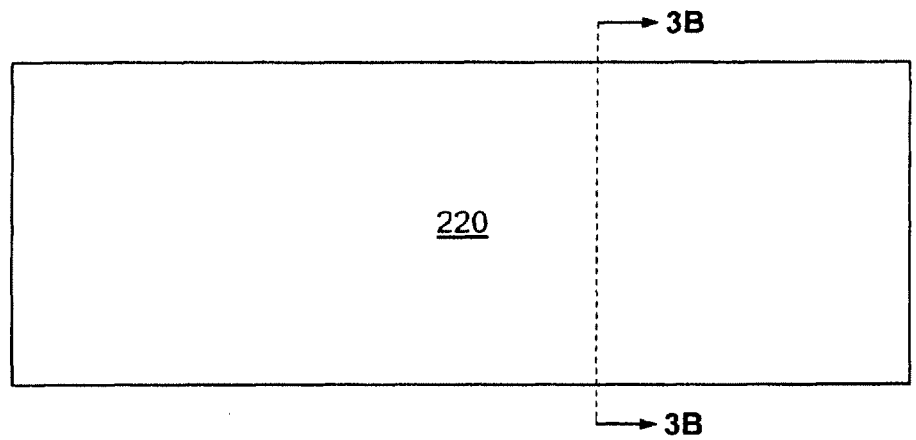
FIGS. 3a-3h is a sequence of steps in forming an electrochemical test sensor according to one process.
Figure 3B:
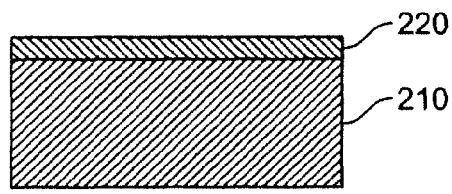
Figure 3C:
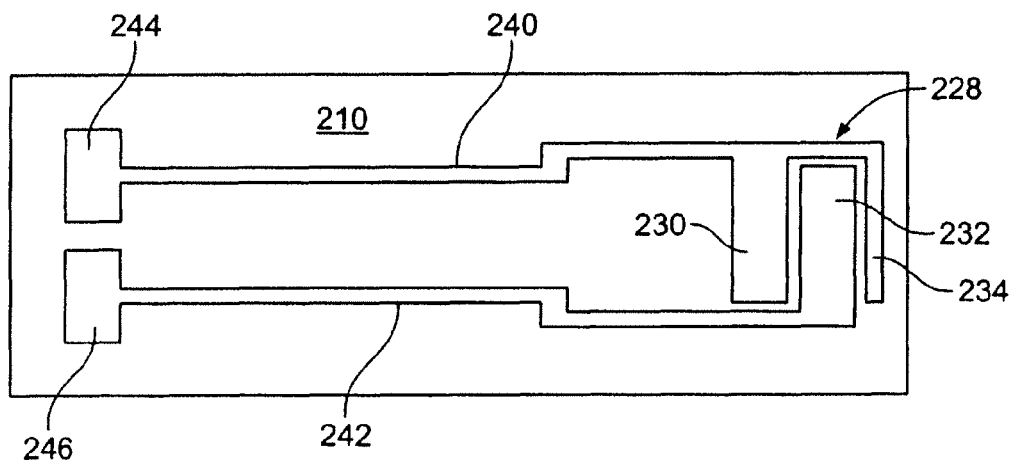

Referring to FIG. 3a-3h, a method of forming an electrochemical test sensor 200 is depicted. Referring to FIGS. 3a, 3b, a base or substrate 210 is shown in which an electrochemically-active material 220 has been placed thereon. As shown in FIG. 3a, the electrochemically-active material 220 covers the entire base 210 in this embodiment. Referring to FIG. 3c, the electrochemically-active material 220 is laser-ablated to form an electrode pattern 228. The electrode pattern 228 includes a plurality of electrodes. More specifically, the electrode pattern 228 includes a counter electrode 230, a working electrode 232, and a trigger electrode 234. A portion of the electrochemically-active material 220 remaining after the laser-ablating act forms a plurality of conductive leads 240, 242 and a plurality of test-sensor contacts 244, 246. The conductive leads 240, 242 assist in establishing electrical communication between the electrodes and the test-sensor contacts 244, 246. The test-sensor contacts 244, 246 are electrically connected with meter contacts (not shown) and assist in conveying information of the analyte to the meter to assist in, for example, determining the analyte concentration.

Figure 3D:
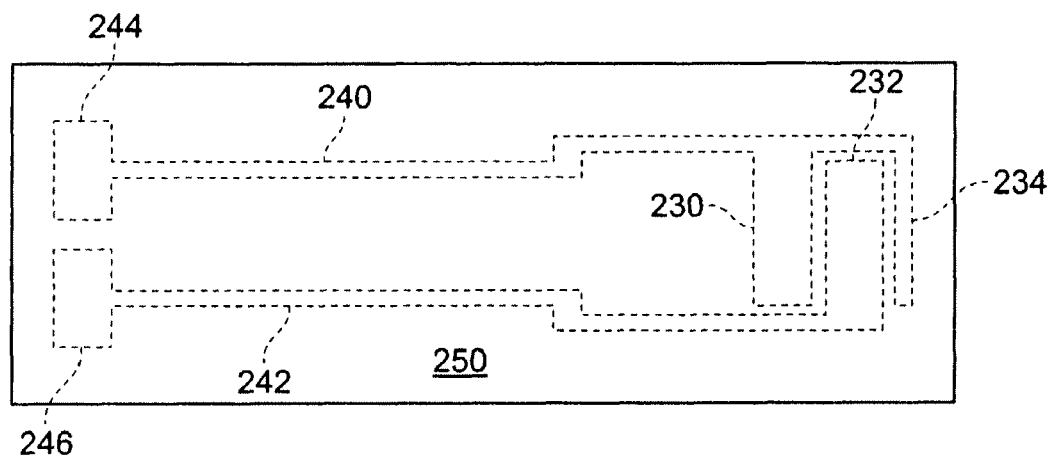
Figure 3E:
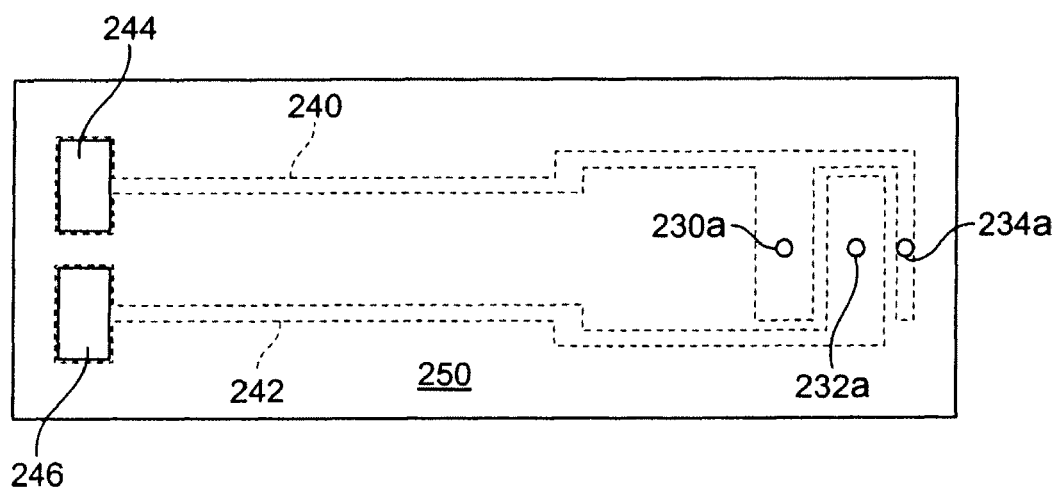
Figure 3F:
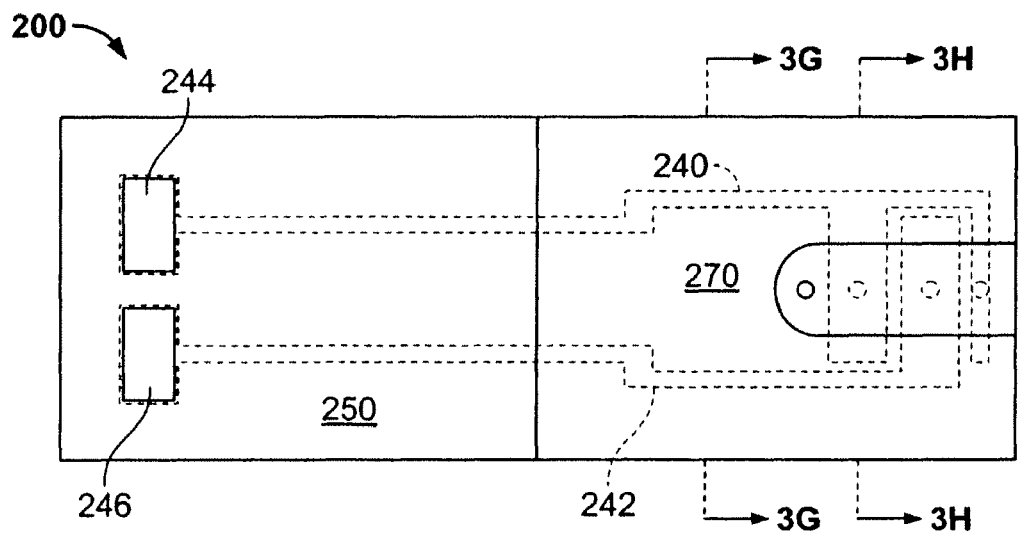
Figure 3G:
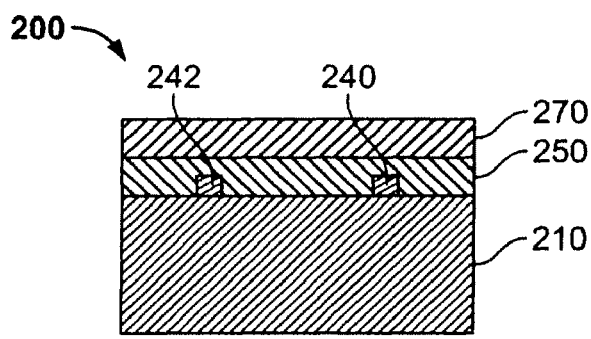
Figure 3H:
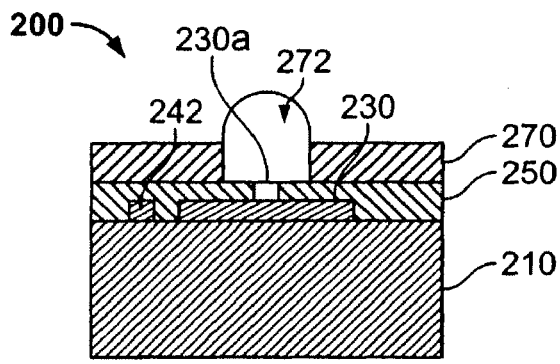

In this method, after the electrode pattern 228 is formed, a dielectric material 250 is placed over the electrode pattern as depicted in FIG. 3d. The dielectric material 250 insulates the electrode pattern 228. Referring to FIG. 3e, selected areas of the dielectric material 250 are laser ablated to expose at least a portion of the electrodes. The exposed electrode patterns are shown as generally circular areas 230a, 232a, 234a in FIG. 3e. It is contemplated that other polygonal or non-polygonal shapes of the electrodes may be exposed by the laser ablation. In FIG. 3e, the dielectric material 250 in this process is also laser ablated to expose the test-sensor contacts 244, 246. Thus, in this method, two separate and distinct laser-ablation acts are performed. After the exposure of the electrodes in the second laser-ablation act, a second layer is applied. For example, in FIGS. 3f-3h, a lid 270 is attached to the dielectric material 250 and forms an opening 272 (see FIG. 3h) to receive a fluid.

Figure 4A:
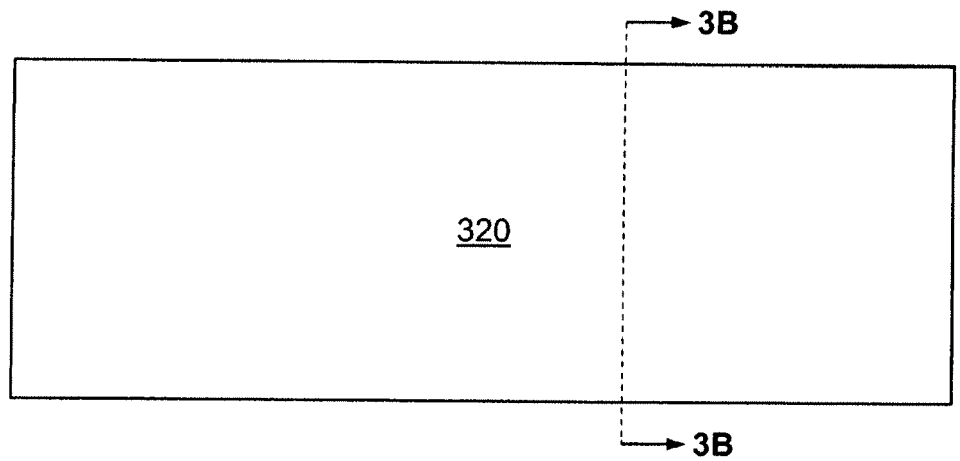
FIGS. 4a-4i is a sequence of steps in forming an electrochemical test sensor with a spacer according to one process.
Figure 4B:
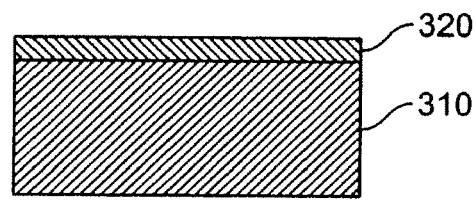
Figure 4C:
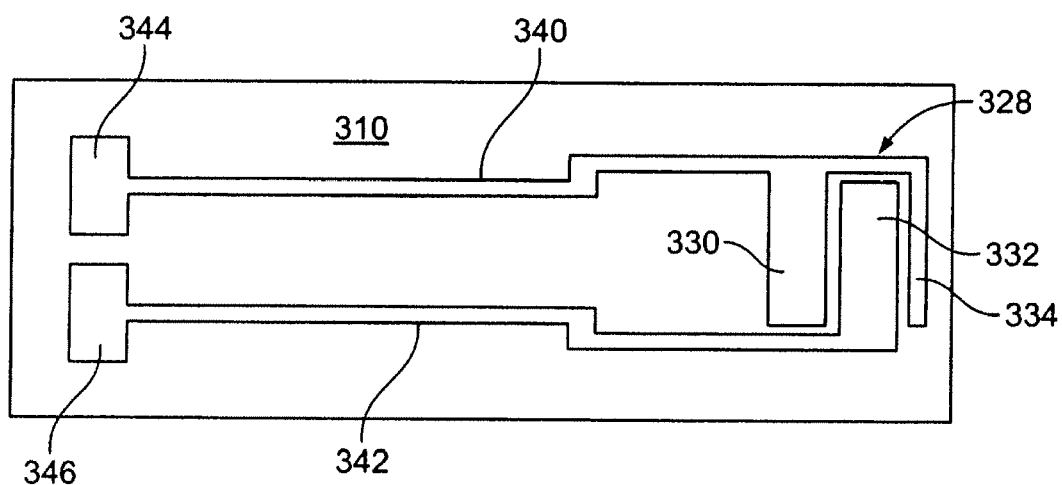

Referring to another method, an electrochemical test sensor 300 is formed in FIGS. 4a-4i. Referring to FIGS. 4a, 4b, a base or substrate 310 is shown in which an electrochemically-active material 320 has been placed thereon. As shown in FIG. 4a, the electrochemically-active material 320 covers the entire base 310 in this embodiment. Referring to FIG. 4c, the electrochemically-active material 320 is laser-ablated to form an electrode pattern 328. The electrode pattern 328 includes a plurality of electrodes. More specifically, the electrode pattern 328 includes a counter electrode 330, a working electrode 332, and a trigger electrode 334. A portion of the electrochemically-active material 320 remaining after the laser-ablating act forms a plurality of conductive leads 340, 342 and a plurality of test-sensor contacts 344, 346. The conductive leads 340, 342 assist in establishing electrical communication between the electrodes and the test-sensor contacts 344, 346. The test-sensor contacts 344, 346 are electrically connected with meter contacts (not shown) and assist in conveying information of the analyte to the meter to assist in, for example, determining the analyte concentration.

Figure 4D:
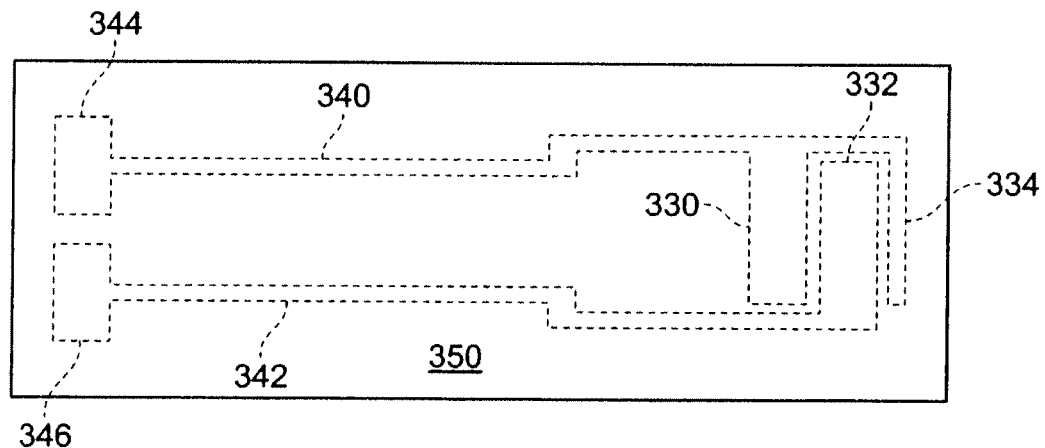
Figure 4E:
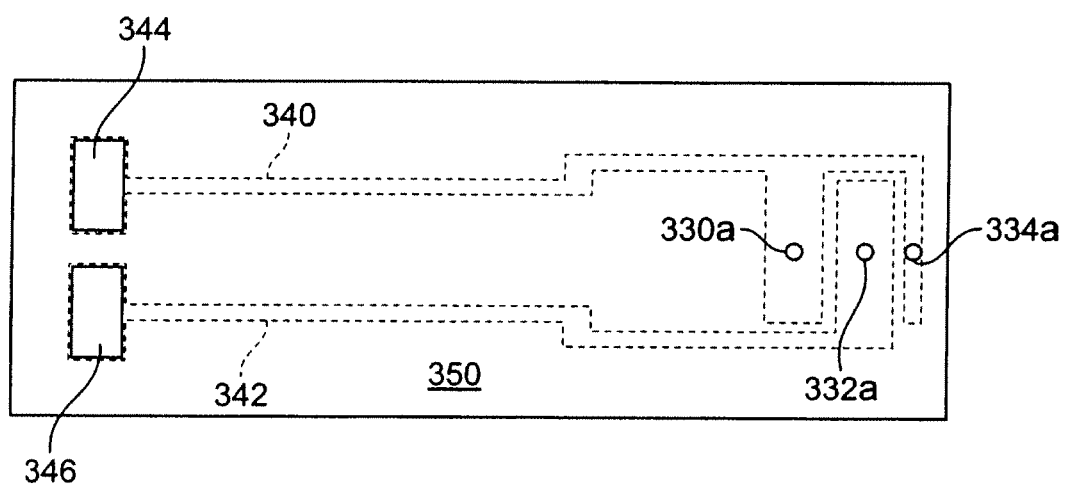
Figure 4F:
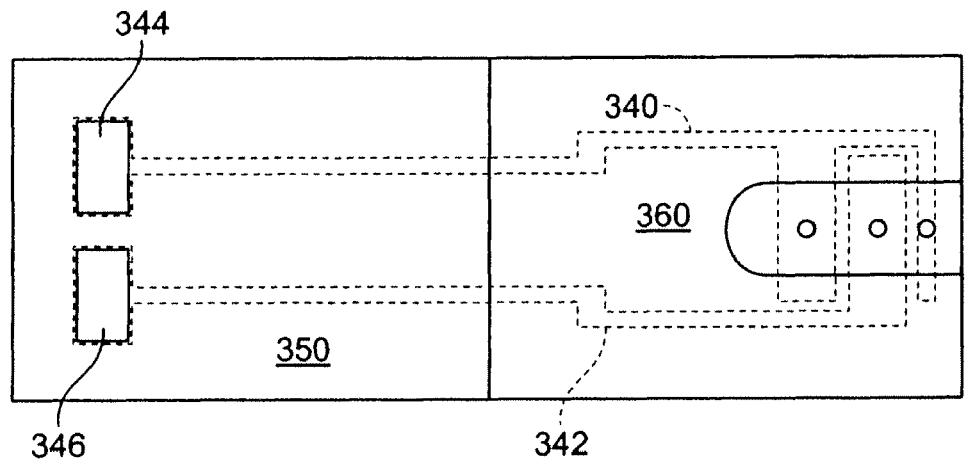

In this method, after the electrode pattern 328 is formed, dielectric material 350 is placed over the electrode pattern as depicted in FIG. 4d. The dielectric material 350 insulates the electrode pattern 328. Referring to FIG. 4e, selected areas of the dielectric material 350 are laser ablated to expose at least a portion of the electrodes. In FIG. 4e, the dielectric material 350 in this process is also laser ablated to expose the test-sensor contacts 344, 346. The exposed electrode portions are shown as generally circular areas 330a, 332a, 334a in FIG. 4e. It is contemplated that other polygonal and non-polygonal shapes of the electrodes may be exposed by the laser ablation as well as forming multiple patterns on one electrode.

Figure 4G:
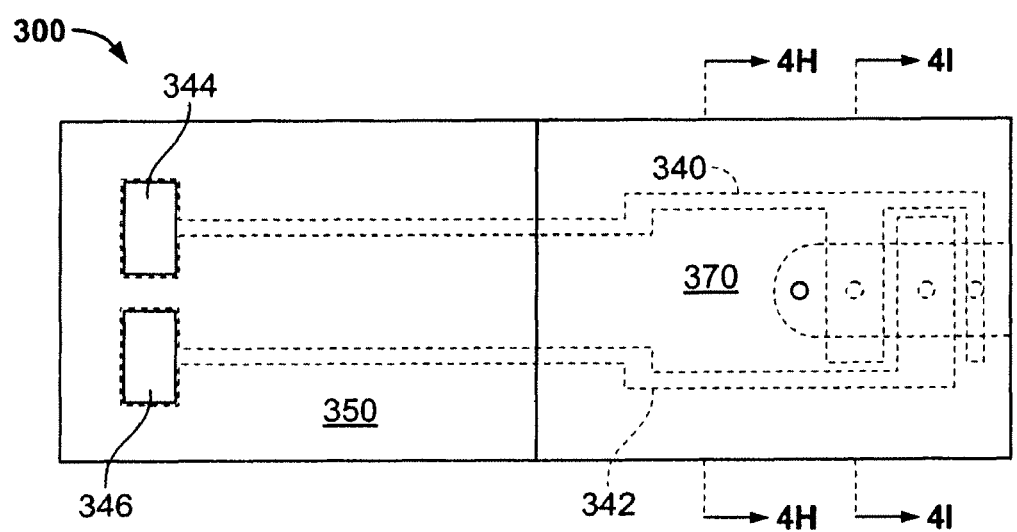
Figure 4H:
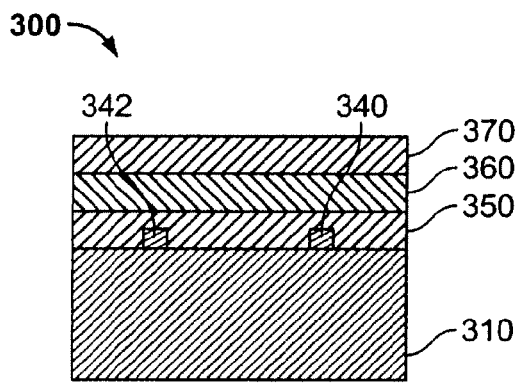
Figure 4I:
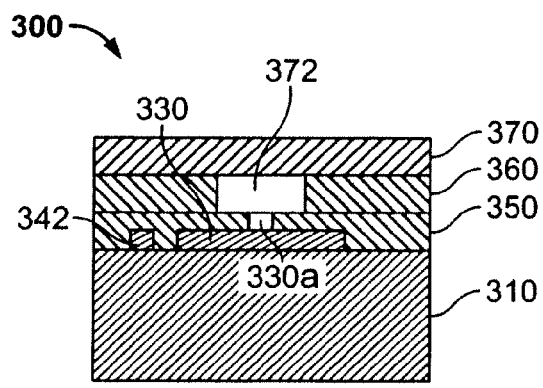

In this method, two separate and distinct laser-ablation acts are performed. After the exposure of the electrodes in the second laser-ablation act, a second layer is applied. For example, in FIG. 4f, a spacer 360 is attached to the dielectric material 350. In FIG. 4g, a lid 370 is attached to the spacer 360. The lid 370, the spacer 360 and the dielectric material 350 assist in forming an opening 372 (see FIG. 4i) to receive a fluid.

Figure 5A:
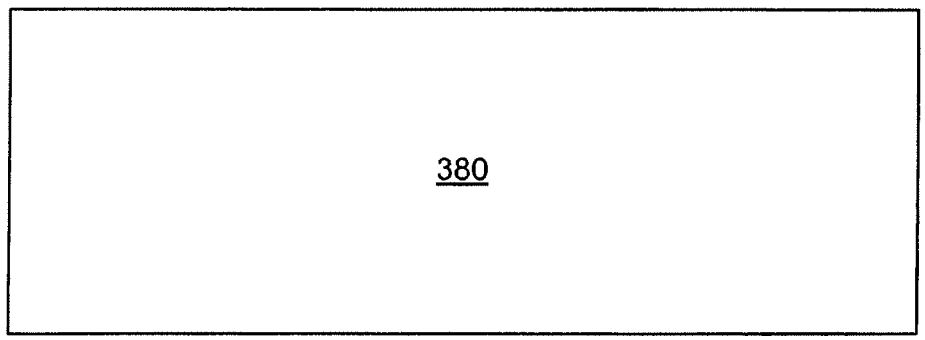
FIGS. 5a, 5b are a few steps in a sequence of steps to be used in forming an electrochemical test sensor according to another process.
Figure 5B:
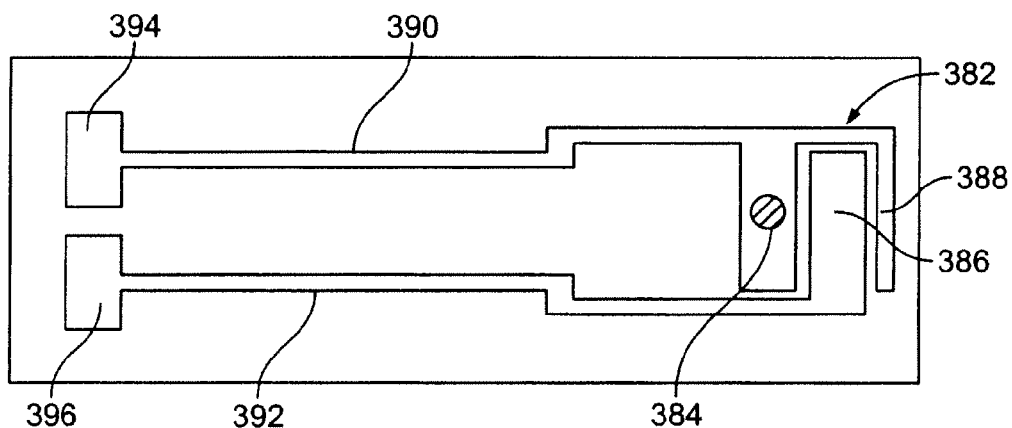

It is contemplated that the plurality of electrodes may be defined on the base by other methods such as, for example, printing (e.g., screen-printing, gravure or ink-jet printing), coating (e.g., reverse roll, slot die), vapor deposition, sputtering and electrochemical deposition. For example, referring to FIG. 5a, a base or substrate 380 may be provided. As shown in FIG. 3b, the electrode pattern 382 may be added to the base 380 by, for example, printing, coating, vapor deposition, sputtering or electrochemical deposition. The electrode pattern 382 includes a plurality of electrodes 384, 386, 388, a plurality of conductive leads 390, 392 and a plurality of test-sensor contacts 394, 396. After the electrode pattern 382 is formed on the base 380, the process may continue by performing the acts discussed above in connection with FIGS. 3d-3h to form an electrochemical test sensor. In another process, after the electrode pattern 382 is formed on the base 380, the process may continue by performing the acts discussed above in connection with FIGS. 4d-4i to form an electrochemical test sensor.

According to another method, an electrochemical test sensor may be formed by initially providing a base or substrate. Electrochemically-active material is placed on the base. Dielectric material is applied over the electrochemically-active material. Thus, in this method an electrode pattern is not created before the dielectric material is applied to the electrochemically-active material. A first selected area of the dielectric material is laser-ablated to expose the electrochemically-active material. A second selected area of the dielectric material is laser ablated and the electrochemically-active material to expose the base. The first selected area is different from the second selected area. A second layer is applied to assist in forming a channel (e.g., capillary channel) in the test sensor. The capillary channel assists in allowing a fluid sample to contact a reagent located therein. The dielectric material is located between the base and the second layer.

Figure 6A:
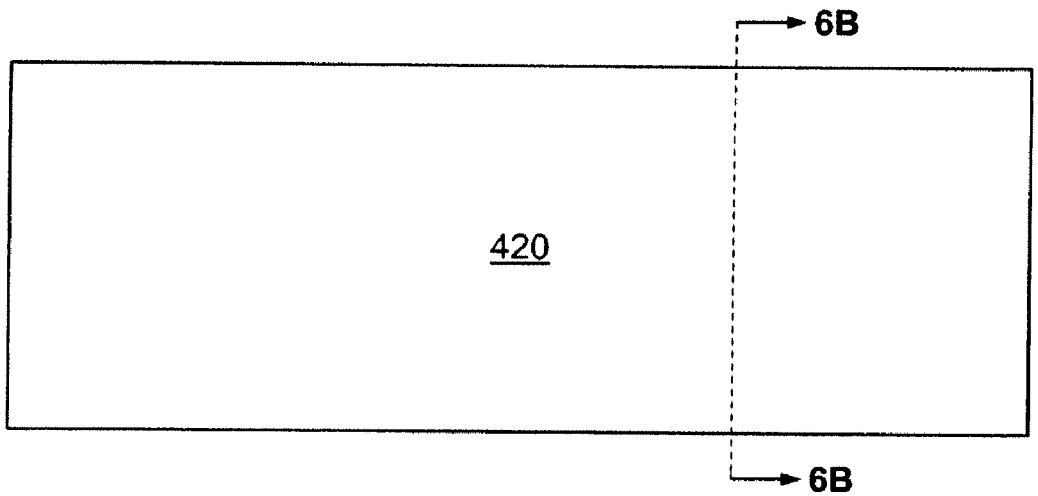
FIGS. 6a-6i is a sequence of steps in forming an electrochemical test sensor according to a further process.
Figure 6B:
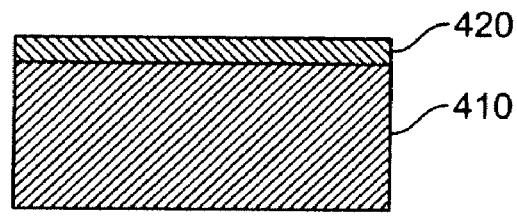
Figure 6C:
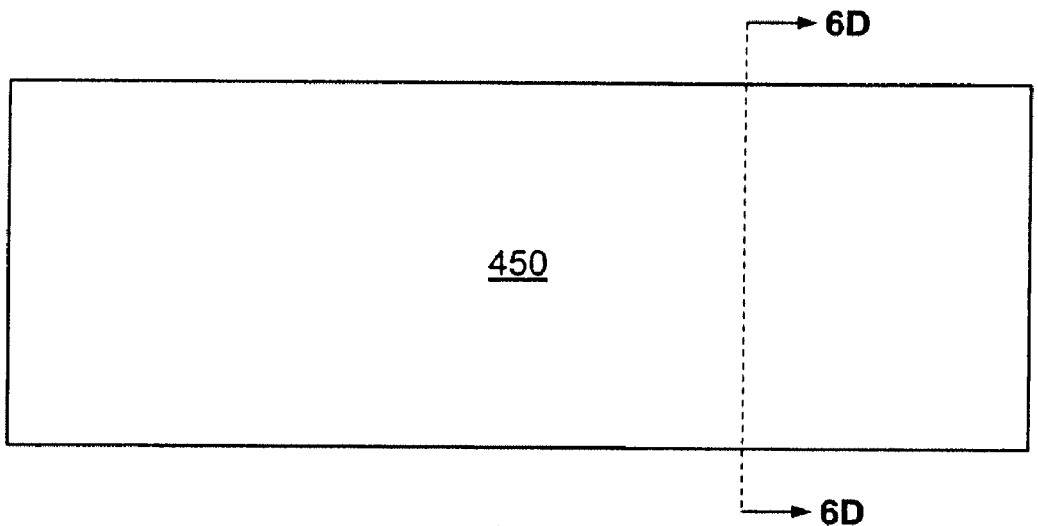
Figure 6D:
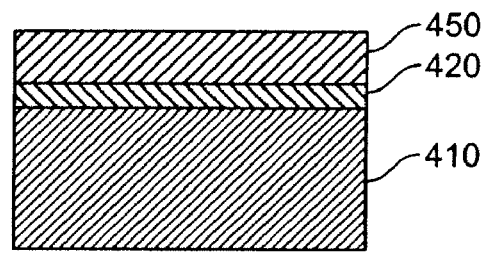

Referring to FIG. 6a-6i, a method of forming an electrochemical test sensor 400 is depicted. Referring to FIGS. 6a, 6b, a base or substrate 410 is shown in which electrochemically-active material 420 has been placed thereon. As shown in FIG. 6a, the electrochemically-active material 420 covers the entire base 410 in this embodiment. Referring to FIGS. 6c, 6d, dielectric material 450 is placed over the electrochemically-active material 420. After the dielectric material 450 is placed over the electrochemically-active material 420, two laser-ablation acts are formed.

Figure 6E:
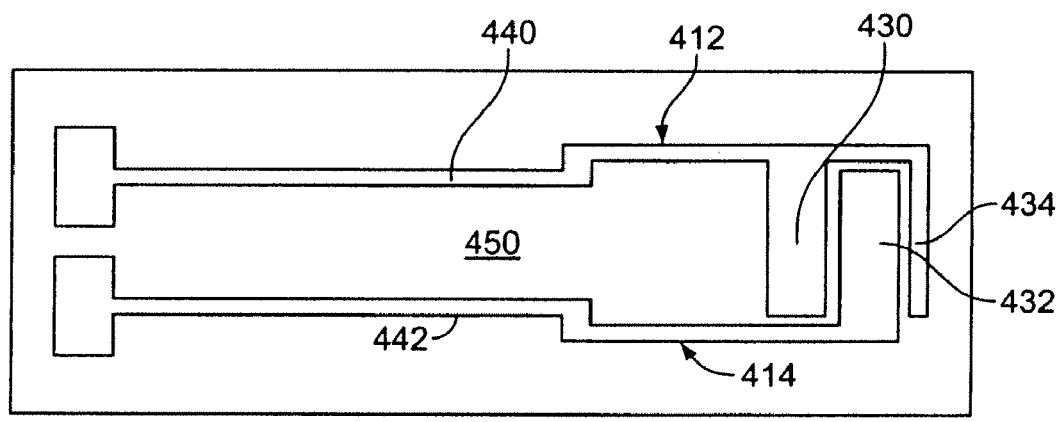

As shown in FIG. 6e, a first laser-ablation act extends through the dielectric material 450 and the electrochemically-active material 420 and forms a plurality of lines 412, 414. Thus, the plurality of lines 412, 414 extends to the substrate 410. The plurality of lines 412, 414 forms outer boundaries of the plurality of electrodes, conductive leads and test-sensor contact boundaries in this embodiment. More specifically, the plurality of electrodes in this embodiment includes a counter electrode 430, a working electrode 432, and a trigger electrode 434. As with the other embodiments, the plurality of electrodes may vary in number. Typically, the plurality of electrodes includes at least working and counter electrodes.

Figure 6F:
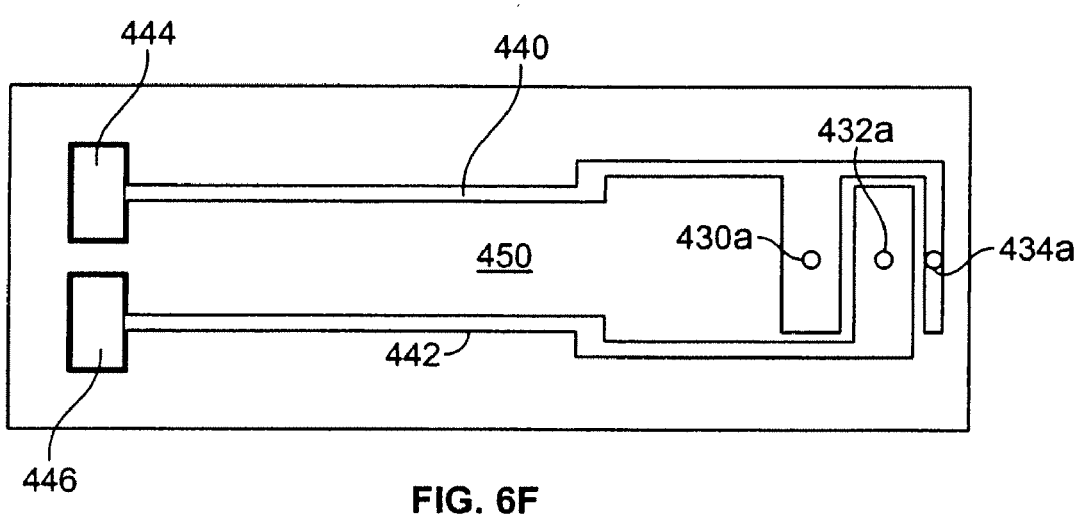
Figure 6G:
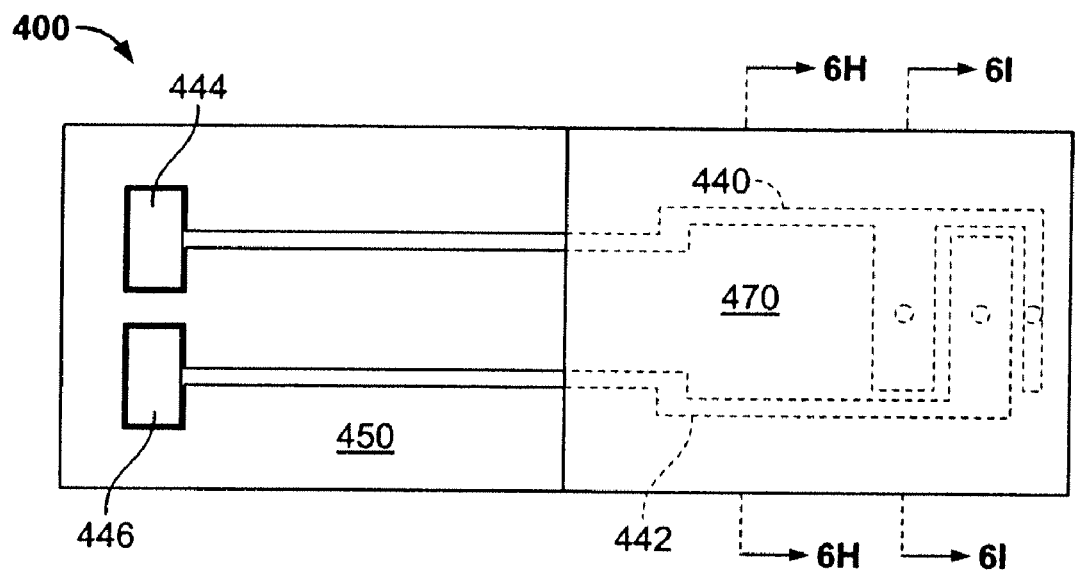
Figure 6H:
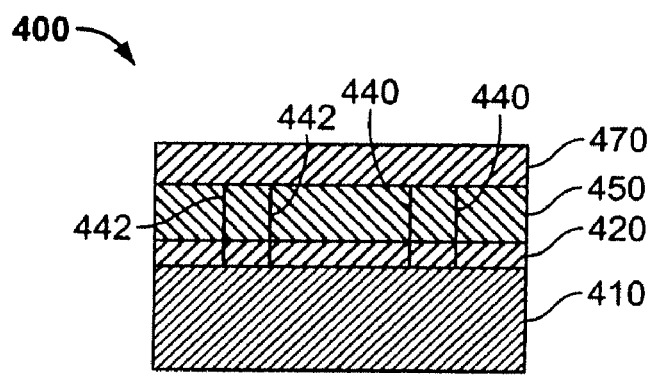
Figure 6I:
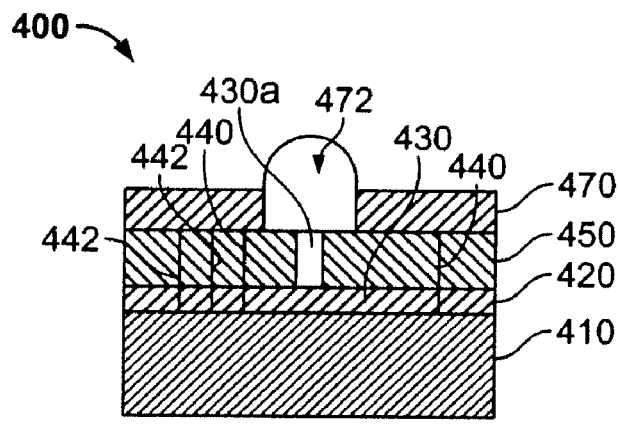

Referring to FIG. 6f, a second laser-ablation act extends only through the dielectric material 450 at selected areas 430a, 432a, 434a that will be exposed to the fluid sample. It is contemplated that the areas 430a, 432a, 434a may be of other shapes than depicted in FIG. 6f. The second laser-ablation act also forms a plurality of test-sensor contacts 444, 446. Thus, the second laser-ablation act extends only to the electrochemically-active material 420. In one method, the first laser-ablation act and the second laser-ablation act are performed using different pulses at different intensities. Thus, the second laser-ablation act may be operated at a lower power intensity. These steps may be performed by multiple lasers, a single laser that includes split beams or a single laser at different times. It is contemplated that the first and second laser ablation acts may be reversed in sequence. For example, the selected area 430a, 432a, 434a may be formed before the plurality of lines 412, 414.

After the exposure of the electrodes in the laser-ablation act, a second layer is applied. For example, in FIGS. 6g-6i, a lid 470 is attached to the dielectric material 450 and forms an opening 472 (see FIG. 6i) to receive a fluid.

Figure 7A:
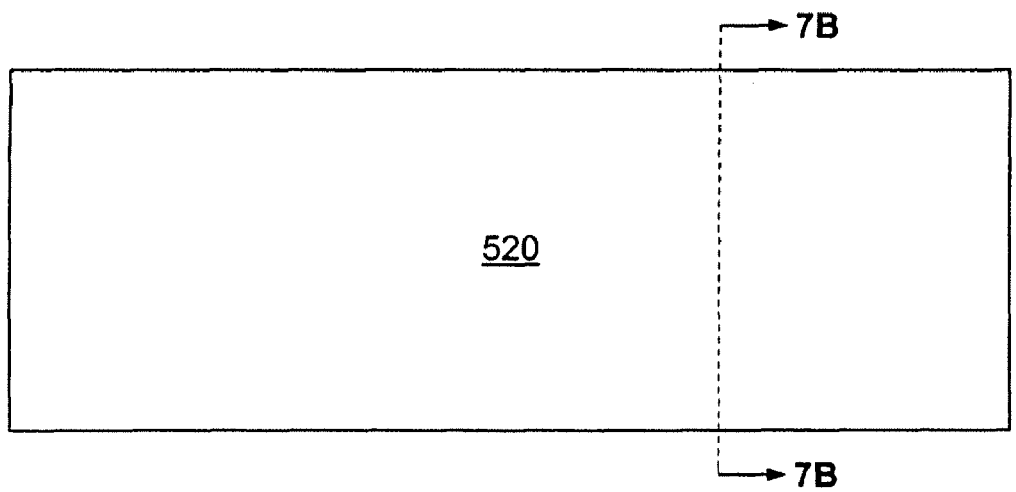
FIGS. 7a-7j is a sequence of steps in forming an electrochemical test sensor with a spacer according to a further process.
Figure 7B:
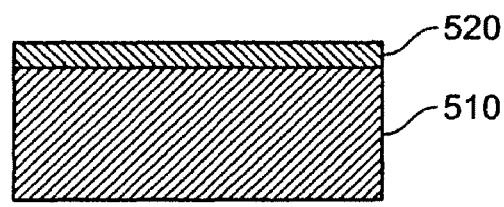
Figure 7C:
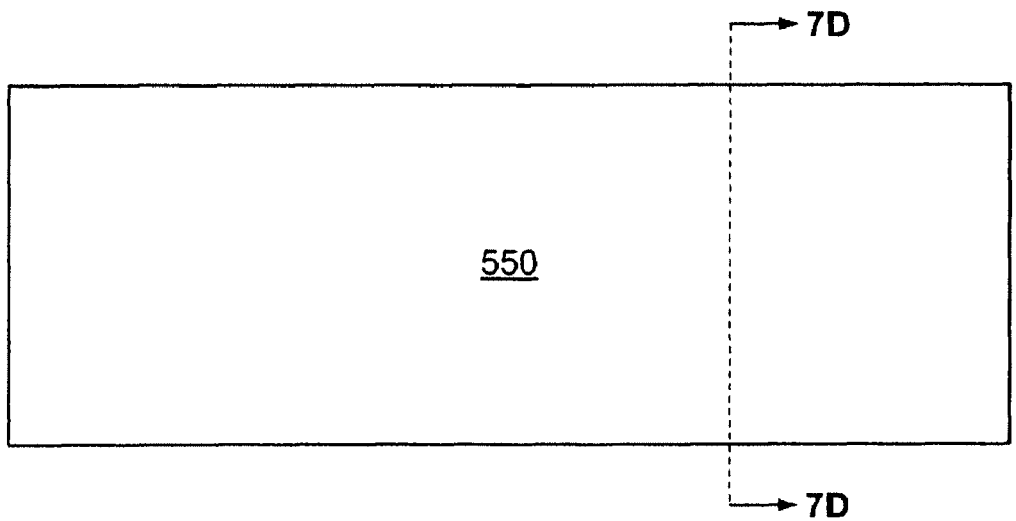
Figure 7D:
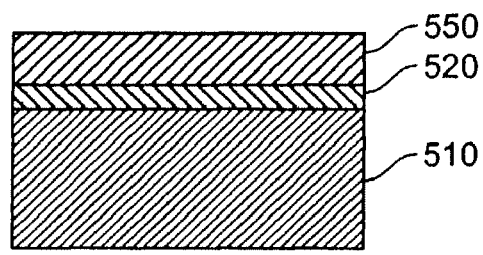

Referring to FIG. 7a-7i, a method of forming an electrochemical test sensor 500 is depicted. Referring to FIGS. 7a, 7b, a base or substrate 510 is shown in which electrochemically-active material 520 has been placed thereon. As shown in FIG. 7a, the electrochemically-active material 520 covers the entire base 510 in this embodiment. Referring to FIGS. 7c, 7d, dielectric material 550 is placed over the electrochemically-active material 520. After the dielectric material 550 is placed over the electrochemically-active material 520, two laser-ablation acts are formed.

Figure 7E:
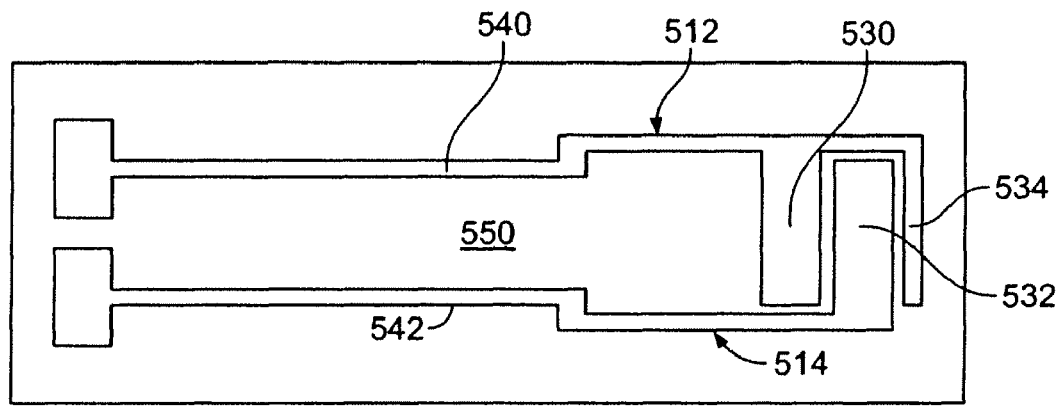

As shown in FIG. 7e, a first laser-ablation act extends through the dielectric material 550 and the electrochemically-active material 520 and forms a plurality of lines 512, 514. Thus, the plurality of lines 512, 514 extends to the substrate 510. The plurality of lines 512, 514 forms outer boundaries of the plurality of electrodes, conductive leads and test-sensor contact boundaries in this embodiment. More specifically, the plurality of electrodes in this embodiment includes a counter electrode 530, a working electrode 532, and a trigger electrode 534. As with the other embodiments, the plurality of electrodes may vary in number. Typically, the plurality of electrodes includes at least working and counter electrodes.

Figure 7F:
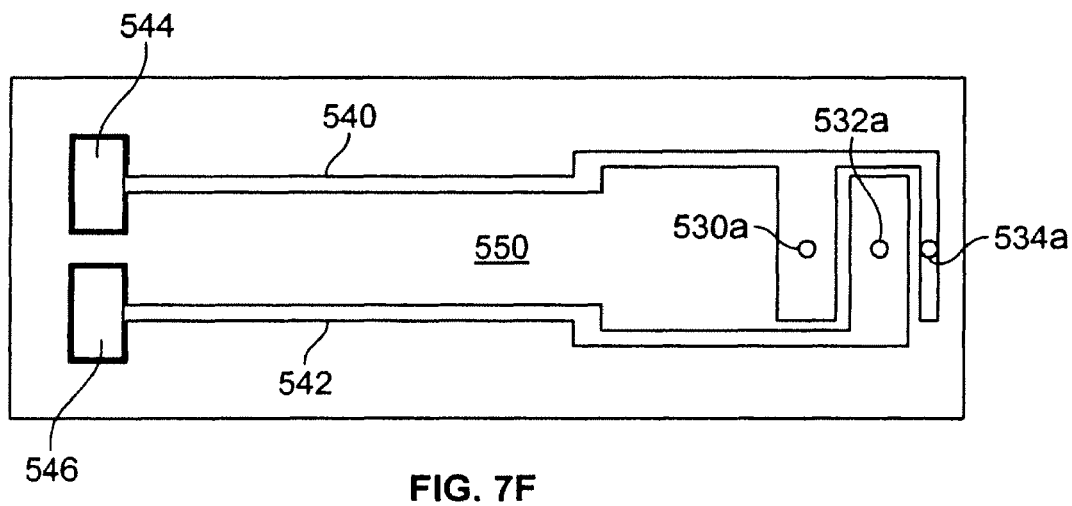

Referring to FIG. 7f, a second laser-ablation act extends only through the dielectric material 550 at selected areas 530a, 532a, 534a that will be exposed to the fluid sample. It is contemplated that the areas 530a, 532a, 534a may be of other shapes than depicted in FIG. 7f. The second laser-ablation act also forms a plurality of test-sensor contacts 544, 546. Thus, the second laser-ablation act extends only to the electrochemically-active material 520. In one method, the first laser-ablation act and the second laser-ablation act are performed using different pulses at different intensities. Thus, the second laser-ablation act may be operated at a lower power intensity. These steps may be performed by multiple lasers, a single laser that includes split beams or a single laser at different times. It is contemplated that the first and second laser ablation acts may be reversed in sequence. For example, the selected area 530a, 532a, 534a may be formed before the plurality of lines 512, 514. After the exposure of the electrodes in the laser-ablation act, a second layer is applied.

Figure 7G:
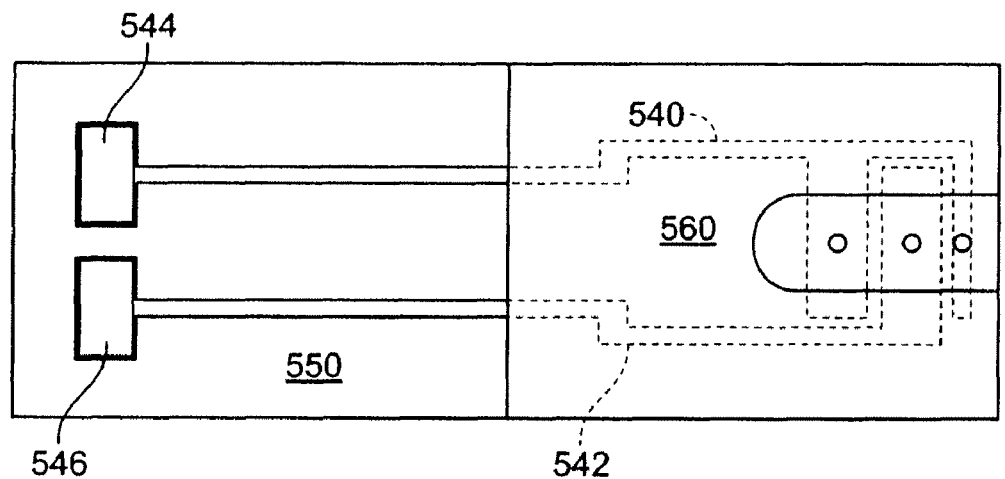
Figure 7H:
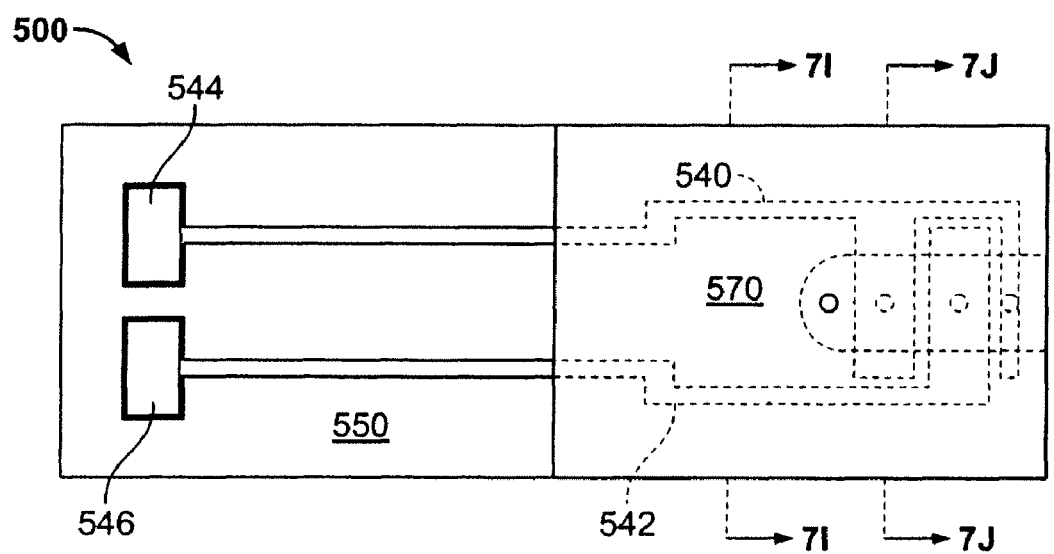
Figure 7I:
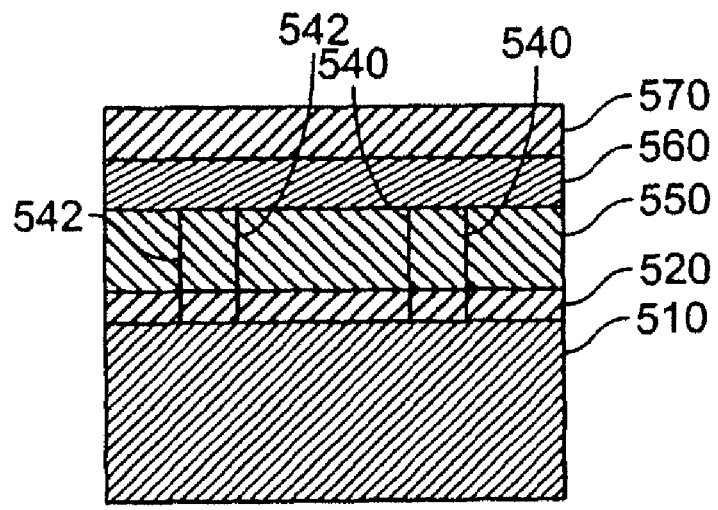
Figure 7J:
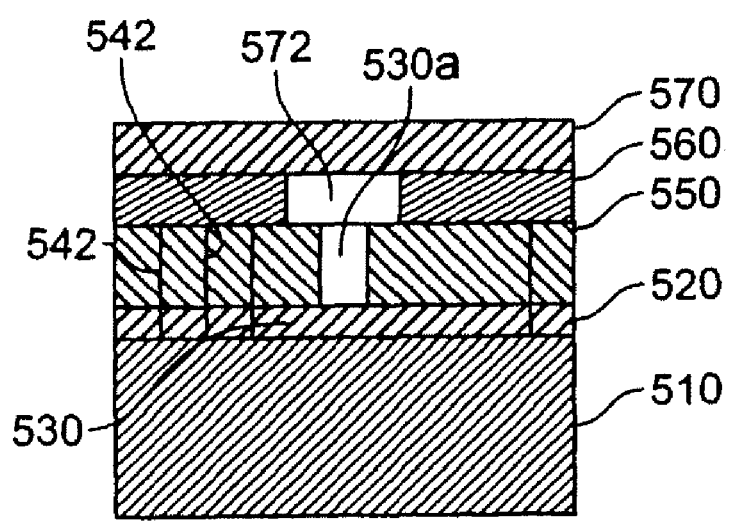

As shown in FIG. 7g, a spacer 560 is added to the dielectric layer 550. As shown in FIGS. 7h-7j, a lid 570 is attached to the spacer 560 and the lid 570, spacer 560 and the dielectric material 550 assist in forming an opening 572 (see FIG. 7j) to receive a fluid.

Process A

A method of forming an electrochemical test sensor, the method comprising the acts of:
  providing a base;
  placing electrochemically-active material on the base;
  laser-ablating the electrochemically-active material to form an electrode pattern;
  applying dielectric material over the electrode pattern;
  laser-ablating selected areas of the dielectric material to expose a portion of the electrode pattern; and
  applying a second layer to assist in forming a channel in the test sensor, the channel assisting in allowing a fluid sample to contact a reagent located therein,
  wherein the dielectric material is located between the base and the second layer.

Process B

The method of alternative process A wherein the laser-ablating of the selected areas further exposes meter contacts on the test sensor.

Process C

The method of alternative process A wherein the second layer is a lid.

Process D

The method of alternative process A wherein the second layer is a spacer and further includes applying a lid to the spacer so as to define the channel, the spacer being located between the lid and the base.

Process E

The method of alternative process A wherein the second layer is a spacer-lid combination.

Process F

The method of alternative process A wherein the electrochemically-active material is a metallic conductive material.

Process G

The method of alternative process A wherein the reagent includes glucose oxidase or glucose dehydrogenase.

Process H

The method of alternative process A wherein the channel is a capillary channel.

Process I

A method of forming an electrochemical test sensor, the method comprising the acts of:
  providing a base;
  forming an electrode pattern on the base;
  applying dielectric material over the electrode pattern;
  laser-ablating selected areas of the dielectric material to expose a portion of the electrode pattern; and
  applying a second layer to assist in forming a channel in the test sensor, the channel assisting in allowing a fluid sample to contact a reagent located therein,
  wherein the dielectric material is located between the base and the second layer.

Process J

The method of alternative process I wherein the electrode pattern is formed by printing, coating, vapor deposition, sputtering or electrochemical deposition.

Process K

The method of alternative process J wherein the electrode pattern is formed by printing.

Process L

The method of alternative process I wherein the second layer is a lid.

Process M

The method of alternative process I wherein the second layer is a spacer and further includes applying a lid to the spacer so as to define the channel, the spacer being located between the lid and the base.

Process N

The method of alternative process I wherein the second layer is a spacer-lid combination.

Process O

A method of forming an electrochemical test sensor, the method comprising the acts of:
  providing a base;
  placing electrochemically-active material on the base;
  applying dielectric material over the electrochemically-active material;
  laser-ablating a first selected area of the dielectric material to expose the electrochemically-active material;
  laser-ablating a second selected area of the dielectric material and the electrochemically-active material to expose the base, the first selected area being different from the second selected area; and
  applying a second layer to assist in forming a channel in the test sensor, the channel assisting in allowing a fluid sample to contact a reagent located therein,
  wherein the dielectric material is located between the base and the second layer.

Process P

The method of alternative process O wherein the laser-ablating of the selected areas further exposes meter contacts on the test sensor.

Process O

The method of alternative process O wherein the second layer is a lid.

Process R

The method of alternative process O wherein the second layer is a spacer and further includes applying a lid to the spacer so as to define the channel, the spacer being located between the lid and the base.

Process S

The method of alternative process O wherein the second layer is a spacer-lid combination.

Process T

The method of alternative process O wherein the electrochemically-active material is a metallic conductive material.

Process U

The method of alternative process O wherein the reagent includes glucose oxidase or glucose dehydrogenase.

Process V

The method of alternative process O wherein the channel is a capillary channel.

While the present invention has been described with reference to one or more particular embodiments, those skilled in the art will recognize that many changes may be made thereto without departing from the spirit and scope of the present invention. Each of these embodiments, and obvious variations thereof, is contemplated as falling within the spirit and scope of the invention.

What is claimed is:

1. A method of forming an electrochemical test sensor, the method comprising the acts of:
providing a base;
placing electrochemically-active material on the base;
applying dielectric material over the electrochemically-active material;
laser-ablating a first selected area of the dielectric material to expose the electrochemically-active material;
laser-ablating a second selected area of the dielectric material and the electrochemically-active material to expose the base, the first selected area being different from the second selected area; and
applying a second layer to assist in forming a channel in the test sensor, the channel assisting in allowing a fluid sample to contact a reagent located therein,
wherein the dielectric material is located between the base and the second layer.

2. The method of claim 1 wherein the laser-ablating of the selected areas further exposes meter contacts on the test sensor.

3. The method of claim 1 wherein the second layer is a lid.

4. The method of claim 1 wherein the second layer is a spacer and further includes applying a lid to the spacer so as to define the channel, the spacer being located between the lid and the base.

5. The method claim 1 wherein the second layer is a spacer-lid combination.

6. The method of claim 1 wherein the electrochemically-active material is a metallic conductive material.

7. The method of claim 1 wherein the reagent includes glucose oxidase or glucose dehydrogenase.

8. The method of claim 1 wherein the channel is a capillary channel.

* * * * *